United States Patent [19]

Lyons et al.

[11] Patent Number: 4,602,104

[45] Date of Patent: Jul. 22, 1986

[54] CATALYTIC OXIDATION OF PROPYLENE TO ALLYL ACETATE

[75] Inventors: James E. Lyons, Wallingford; George Suld, Springfield, both of Pa.

[73] Assignee: Sun Refining and Marketing Company, Philadelphia, Pa.

[21] Appl. No.: 722,094

[22] Filed: Apr. 10, 1985

Related U.S. Application Data

[63] Continuation-in-part of Ser. No. 664,565, Oct. 29, 1984, abandoned, which is a continuation-in-part of Ser. No. 559,140, Dec. 7, 1983, abandoned.

[51] Int. Cl.⁴ .............................................. C07C 67/05
[52] U.S. Cl. ..................................................... 560/243
[58] Field of Search ................................. 560/243, 245

[56] References Cited

U.S. PATENT DOCUMENTS

| | | | |
|---|---|---|---|
| 3,275,680 | 9/1966 | Holzrichter | 560/243 |
| 3,600,429 | 8/1971 | Kronig | 560/243 |
| 3,925,452 | 12/1975 | Swodenk | 560/245 |
| 3,960,930 | 6/1976 | Clarke | 560/243 |
| 3,970,713 | 7/1976 | Scharfe | 560/245 |

FOREIGN PATENT DOCUMENTS

| | | | |
|---|---|---|---|
| 45-4965 | 2/1970 | Japan | 560/243 |
| 1101224 | 1/1968 | United Kingdom | 560/243 |
| 1247595 | 9/1971 | United Kingdom | 560/245 |
| 1251831 | 11/1971 | United Kingdom | 560/243 |

*Primary Examiner*—Michael L. Shippen
*Attorney, Agent, or Firm*—J. Edward Hess; Donald R. Johnson; Stanford M. Back

[57] ABSTRACT

Propylene is oxidized directly to allyl acetate in the presence of acetic acid with air or oxygen in the liquid phase under moderate reaction conditions employing a palladium-on-carbon catalyst which has been pretreated by activating it with propylene at temperatures of greater than about 50° C., preferably from 60° to 150° C., for a period of time sufficient to form a small but perceptible quantity of said activated catalyst, preferably for at least 10 minutes in the substantial absence of oxygen.

30 Claims, No Drawings

CATALYTIC OXIDATION OF PROPYLENE TO ALLYL ACETATE

CROSS-REFERENCE TO RELATED CASES

This application is a continuation-in-part of U.S. application Ser. No. 664,565, filed Oct. 29, 1984, now abandoned, which in turn is a continuation-in-part of U.S. application Ser. No. 559,140, filed Dec. 7, 1983, now abandoned, in the name of Lyons et al.

The subject matter of this invention is related to that of Ser. No. 721,817, filed Apr. 10, 1985 in the name of Lyons et. al., and entitled "Catalytic Oxidation of Olefins to $\alpha,\beta$-Unsaturated Carboxylic Acids".

BACKGROUND OF THE INVENTION

1. FIELD OF THE INVENTION

This invention relates to a process for the oxidation of propylene to form allyl acetate, a specialty chemical useful as a precursor to allyl alcohol and other articles of commerce. More particularly, this process is directed to the improvement of oxidizing propylene in one step in the presence of acetic acid to form allyl acetate at high selectivities and yields under moderate reaction conditions in the liquid phase by the use of a novel olefin-activated palladium catalyst.

2. DESCRIPTION OF THE PRIOR ART

The literature reports that palladium catalysts of several different types promote the oxidation of propylene to allyl acetate in the presence of acetic acid. One type of catalyst is a silica-supported palladium catalyst (U.S. Pat. No. 3,925,452) which requires elevated temperature (>140° C.) and produces carbon dioxide as the major by-product. A stoichiometric oxidant—$PdCl_2$, together with large amounts of sodium acetate (*J.A.C.S.*, 98,6913 (1976)) operates in the liquid phase at low temperature (25°–100° C.) but produces 2-acetoxypropene as a significant by-product. Typical soluble palladium and copper chloride and acetate catalyst systems give very poor allyl acetate selectivity when used in acetic acid in the presence of acetate ion (Clark, Hayden and Smith, *Discuss. Faraday Soc.*, 46 98 (1968)). Another type of catalyst, palladium trifluoroacetate, operates under mild conditions in the liquid phase to give allyl acetate as the predominant product (French Patent No. 79-05874 (1980)) but catalyst recovery for re-use is difficult. Thus, allyl acetate has been prepared by heterogeneous catalysts in the vapor phase at high temperature or by a soluble catalyst in the liquid phase at low temperature. In the former case reaction selectivity is a problem and in the latter case both selectivity and catalyst recovery are major difficulties.

In addition, Hinnenkamp, U.S. Pat. No. 4,435,598; Scharfe, U.S. Pat. No. 3,970,713; Onoda, U.S. Pat. No. 4,016,200; and Slesser, British Pat. No. 1,251,831 teach conventional methods for oxidizing olefins in the presence of palladium catalysts, wherein said catalysts are prepared by reducing palladium salts with various reducing agents including olefins under routine reduction conditions. Scharfe, whose catalyst is impregnated with potassium acetate for use in oxidizing propylene to allyl acetate, additionally makes the obvious point that it is commercially advantageous, although not essential, to carry out the reduction before introducing the volumes of oxygen needed for oxidation. Nowhere, however, is there any recognition of preparing the catalyst in the substantial absence of oxygen, or the benefits to be derived therefrom. Similarly, Hartley, "The Chemistry of Platinum and Palladium," Wiley and Sons, pp. 386–390 and 412–417 (1973) discloses a method for making a palladium chloride catalyst complexed with ethylene for use in the acetylation of olefins to vinylic acetates. However, none of these prior art teachings disclose the use of a unique olefin-activated palladium metal catalyst as defined herein to prepare allyl acetate from propylene.

Finally, Holzrichter, U.S. Pat. No. 3,275,680, teaches oxidizing propylene to allyl acetate in the presence of acetic acid and a palladium catalyst. However, a totally different catalyst system than is claimed hereinbelow, prepared by the reduction of palladium salts with hydrazine, is taught. Moreover, the ultimate conversion of propylene, and yields per pass, are relatively low.

Therefore, it is an object of this invention to provide an improved process for converting propylene to allyl acetate in one step at high yields and selectivities, as contrasted with reported prior art methods, utilizing an easily recovered heterogeneous catalyst in the liquid phase under mild conditions.

Other objects of this invention will be evident from the description and examples set forth hereinbelow.

SUMMARY OF THE INVENTION

In accordance with the present invention it has now been found that propylene can be oxidized with air or oxygen in the presence of acetic acid in a single step in the liquid phase and under mild reaction conditions to form allyl acetate in high yield and at high selectivities when there is employed an activated palladium metal catalyst supported on carbon or alumina, wherein the palladium has been activated with a $C_3$–$C_6$ olefin, preferably propylene, prior to said oxidation under conditions described in detail below. By this unique expedient, catalysts which were otherwise inactive at temperatures below 60° C. are now not only active for this purpose at much lower temperatures, i.e. greater than about 25° C., but also they provide molar selectivities to allyl acetate approaching 100%, thus virtually eliminating the formation of undesired $CO_2$.

DESCRIPTION OF THE PREFERRED EMBODIMENTS

The general method of oxidizing propylene to allyl acetate is adequately described in the above-described prior art and need not be described herein in detail. Suffice it to say that utilizing the catalyst of this invention, prepared by the novel method discussed in detail below, the oxidation reaction of propylene to allyl acetate in the presence of acetic acid can then be uniquely carried out at temperatures as low as about 25° C., up to about 125° C., and at pressures of about 1 to 100 atm. Preferably, temperatures of from 25° to 85° C., and pressures of from about 1 to 10 atm. may be employed, as contrasted with the much more rigorous conditions employed in U.S. Pat. No. 3,624,147. Moreover, as a consequence of this new catalyst, rates, selectivities, and thus yields, are significantly increased.

In one preferred emodiment of this process, in order to increase the reaction rate and at the same time reduce the reactor volume, it has been found to be advantageous that the reaction be carried out in a trickle bed reactor in which the liquid reaction medium is allowed to pass downward over a fixed catalyst bed and the allyl acetate product recovered at the bottom. Alternatively, the oxidation reaction can be carried out using an ebulating bed of catalyst while circulating gases and solvent.

As described in copending application Ser. No. 721,817, the catalyst employed in this invention may be prepared by activating a carbon- or alumina-supported palladium metal catalyst with a $C_3$–$C_6$ olefin, preferably propylene. The starting material from which the catalyst is prepared may be any finely divided palladium in the metallic state, on a support such as carbon or, less preferred, alumina, as for example a commercially available 5%, 10%, or 20% palladium on carbon available from standard catalyst manufacturers such as Engelhard Industries or Johnson Mathey, Inc. By the terms "palladium metal catalyst" or "palladium in the metallic state" is meant those palladium catalysts which have been prepared from their salts or like compounds by known reduction means either commercially or as shown, for example, by Scharfe et al, U.S. Pat. No. 3,970,713, or Holzrichter et al, U.S. Pat. No. 3,275,680, but which have simultaneously or subsequently been exposed to oxygen or the atmosphere in normal course of preparing and handling the same. While applicants do not wish to be bound by any particular theories, it is believed that in the normal course of preparing, handling and using the reduced catalysts of the prior art subsequent to reduction of the palladium, a certain proportion of the palladium surface species, by virtue of exposure to oxygen or the atmosphere, becomes at least partly oxidized. It is this oxidized form of palladium metal catalyst which is now being employed as the starting material in the preparation of the olefin-activated catalyst employed herein. (By "surface species", as recognized by those skilled in the catalyst art, is meant any species of palladium found at the surface of the catalyst per se.)

Again, while applicants do not wish to be bound by any particular theory, it is believed that when this partly oxidized palladium surface, as described above, is contacted with propylene in accordance with applicants' invention, it is first converted to highly active palladium metal sites having zero valence, and it is with these sites that the propylene then forms the novel surface-active species which is the activated catalyst used in this invention.

As evidence that the commercially-reduced palladium, for example, has formed oxidized sites on its surface under normal preparation, handling and exposure to air, it has been found that in the course of preparing the novel activated catalyst of this invention, starting, e.g., with a commercially reduced palladium metal catalyst, under oxygen-free conditions in water, two parts propylene employed in activating the catalyst result in the formation of one part acetone and one part active catalyst species.

In preparing the novel activated oxidation catalyst of this invention by treating a carbon- or alumina-supported palladium metal catalyst as defined above with propylene or like olefins, it is essential that this activation treatment be carried out under oxygen-free conditions, as described below. Because little or no activation appears to take place below about 50° C., it is also necessary that this activation be conducted at temperatures of greater than about 50° C., desirably from about 55° C. to about 150° C., and preferably from about 60° to 95° C., for a period of time sufficient to provide at least a small but perceptible quantity of said activated catalyst, i.e. one which is highly effective for oxidizing propylene at temperatures of about 25° C. and above. While the time necessary to activate the catalyst is not critical, and will depend upon its nature and amount, generally, periods of at least about 10 minutes, preferably at least about 30 minutes are necessary to produce activation, as defined below. This activation is desirably carried out at pressures of at least about 1 atmosphere, up to about 10 atmospheres of olefin, although about 2–20 atmospheres is preferred. While the activation is desirably conducted in a liquid medium, preferably acetic acid, alternatively it may be carried out in a pure, oxygen-free olefin atmosphere alone, i.e. in the vapor phase. In addition to water or acetic acid, solvents which do not adversely affect the activity of the catalyst may be employed instead.

When these catalysts are thus activated, palladium-on-carbon, for example, which was otherwise far less reactive at temperatures below about 60° C. for purposes of oxidizing propylene is now surprisingly active at temperatures of about 25° C. or above. Moreover, as aforestated, both the rates and selectivities to allyl acetate are significantly improved by this treatment. Thus, by the term "activated palladium metal catalyst" is meant, for purposes of this invention, a catalyst prepared in accordance with the above method.

During the preparation of the catalyst, as stated above, it is important for purposes of deriving maximum activity from the catalyst that the activation be carried out in the substantial absence of oxygen, and preferably under essentially oxygen-free conditions. While the presence of small amounts of oxygen, to an extent which can be readily determined by those skilled in the art, can still result in a catalyst which performs somewhat better than the commercial catalysts described above, the full benefits of the present invention are derived from activating the catalyst under conditions which are as oxygen-free as possible.

These oxygen-free conditions can be achieved by known means, for example by using deaerated water or acetic acid or solvent, and pure olefin gas, during the activation of the catalyst. Deaeration can be readily achieved by placing the liquid under vacuum until it boils, or by bubbling the desired olefin through the liquid for a period of time until no more oxygen is displaced. The pure olefin can be obtained commercially in various grades such as chemical purity grade, research purity grade, or polymer grade, the latter two being preferred because of their higher purity of over about 99.7%. (The latter two are available, for example from Matheson, Division of Searle Medical Products, and Sun Co., respectively.)

Once applicants' catalyst is formed, it is preferable that at least a slight excess of propylene be present at all times to prevent any deactivation, and that desirably during the oxidation step, oxygen in the reactor be maintained in no greater than the stoichiometric amounts needed for the oxidation of the propylene to allyl acetate. It will also be understood that in preparing the catalyst of this invention, the presence of those metals or metal salts which might poison or alter the catalyst should be avoided, for example iron, manganese, copper and rhodium salts; chlorides, benzoquinone, the oxidized form of heteropoly acids, as well as any other agents which would oxidize palladium to palladium$^{+2}$. Other such deleterious materials can be routinely determined by those skilled in the art. For example, in addition, it has been found that such materials as amines, hydrazine, and ethylene should be avoided as deleterious when preparing and using the catalyst of this invention. Moreover, it has been found that attempts to use hydrogen to prepare this catalyst may result in explosions when the catalyst is then exposed to $O_2$-propylene mixtures, and should also be avoided.

While the catalyst of the invention may be prepared separately and maintained in an active state if kept in an oxygen-free atmosphere, more conveniently the preparation is carried out in the same reactor used for the propylene oxidation. This may conveniently be achieved, for example by adding a commercially available finely divided palladium on activated carbon to an acetic acid medium in a sealed reactor, flushing the system with propylene gas, and then heating the mixture under propylene pressure until the desired temperature for preparation of the catalyst is reached, at which time the mixture is stirred for at least about 10 minutes at that temperature, again, in the absence of oxygen, and desirably in the presence of a slight excess of propylene.

After the preparation of the catalyst, the propylene may be replaced by a mixture of propylene and oxygen, desirably with oxygen being present in not more than approximately stoichiometric amounts to avoid deactivation of the catalyst, and the oxidation reaction carried out in the presence of acetic acid at pressures of from about 1 to 10 atmospheres. The pressure may be maintained by the further addition of the gas mixture from time to time until the desired propylene conversion to allyl acetate is achieved. Air may be used in place of oxygen, in which case the amount of propylene must be adjusted proportionately.

While the activating agent for the catalyst is preferably propylene, if desired there may instead be employed other light olefins having an allylic hydrogen and containing from 3-6 carbon atoms. Most preferred, in addition to propylene, are butene-1, butene-2 or isobutylene.

The olefin-activated catalyst will maintain its activity over long periods of time as long as at least small amounts of a $C_3$-$C_6$ olefin are present. Thus, it has been found beneficial to run the reaction by constantly sparging the propylene/oxygen or air reaction mixture through the acetic acid solution. In this way, the propylene is kept in excess and the catalyst remains highly active, thereby maintaining high selectivities and other advantages noted above.

When carrying out the oxidation in a batch-wise manner the ratio of catalyst to reaction medium is desirably in the range of about 0.05-5.0 gram atoms of palladium per liter of reactant, and preferably about 0.1-1.0 gram atoms. In a continuous process utilizing, e.g., a fixed bed reactor, the reaction can be conducted effectively by varying the volume of reactants and contact time with the catalyst in a generally known manner to achieve the high yields and selectivities disclosed herein.

In a further embodiment, it has been discovered that when small amounts of acetic anhydride are also added to the reaction medium, generally in amounts of 5 to 15 wts. per weight of acetic acid, the formation of allyl alcohol is completely suppressed, thereby additionally increasing the yields and selectivities of the allyl acetate.

Likewise, small amounts of a metal acetate such as sodium acetate may be added to the reaction in amounts of up to 0.7 moles per liter of liquid medium for the purpose of enhancing the acetate ion concentration, and also the yield.

When carrying out the oxidation in a batch-wise manner the ratio of catalyst to reaction medium is desirably in the range of about 0.05-5.0 gram atoms of palladium per liter of reaction medium, and preferably about 0.1-1.0 gram atoms. In a continuous process utilizing, e.g., a fixed bed reactor, the reaction can be conducted effectively by varying the volume of reactants and contact time with the catalyst in a generally known manner to achieve the high yields and selectivities disclosed herein.

The following examples are by way of illustration of the invention.

EXAMPLES 1-9

In the following examples, 1-9, a number of reactions were run in accordance with the following general procedures:

One gram of 10% palladium metal on carbon (Engelhard Industries) was added to an 85 ml Fisher-Porter aerosol tube together with sodium acetate in the amounts shown in the Table. Then 30 ml of deaerated glacial acetic acid was added and the Fisher-Porter tube was fitted to a pressure manifold. The mixture was flushed to 50 psi three times with pure propylene gas (research purity grade). It was then heated with stirring under 50 psi of this pure propylene until it reached the desired activation temperature where the mixture was stirred for 30 minutes. The stirred mixture was then brought to the desired reaction temperature and the propylene was replaced with a gas mixture having the composition: 35% $O_2$/65% pure $C_3H_6$ to a total pressure of 100 psig. Reaction proceeded immediately in most cases and the pressure dropped. When the total pressure reached 80 psig the $O_2$/$C_3H_6$ gas mixture was admitted to bring the total pressure to 100 psig. This was repeated as often as necessary during the course of the run. After the determined reaction time the mixture was cooled, the gas captured and analyzed and the mixture filtered. The catalyst was washed with acetic acid to remove small amounts of allyl acetate held on the surface. The filtrates were analyzed by standardized GC to determine the product composition comprising allyl acetate, and isopropenyl acetate by-product.

As shown in Table I above, the conditions for pretreating the catalyst and for oxidizing the propylene to allyl acetate were varied from run to run to better illustrate the scope of the invention.

The table compares activated palladium-on-carbon with standard soluble $Pd(OAc)_2$/$CuCl_2$ catalysts. Examples 1 and 2 show that standard soluble palladium catalysts give poor selectivity to allyl acetate under the reaction conditions of this invention. Examples 3 and 4 show low yields and selectivities using palladium-on-carbon which had not been pre-reduced. Examples 6-9 show high yields of allyl acetate over activated catalysts which improve by increasing the added sodium acetate.

TABLE I

PALLADIUM-CATALYZED OXIDATION OF PROPYLENE TO ALLYL ACETATE, (AA)

| Catalyst (a) | NaOAc moles/l | Activation Time, Min. (d) | Reaction Time Hrs. (d) | Gas Consumed, psi | WT % IN PRODUCT | | SELECT. TO AA, % |
|---|---|---|---|---|---|---|---|
| | | | | | AA | IPA (b) | |
| 1 Pd(OAc)$_2$/CuCl$_2$ | 0.167 | 0 | 4.25 | 161 | >0.4 | 0.75 | >8.0 |
| 2 Pd(OAc)$_2$/CuCl$_2$ | 0.667 | 0 | 4.25 | 225 | 2.33 | 3.36 | 9.1 |
| 3 10% Pd-C | 0.167 | 0 | 5 | 68 | 1.89 | 1.75 | 39.1 |
| 4 10% Pd-C | 0.333 | 0 | 5 | 130 | 5.79 | 1.65 | 69.7 |
| 5 10% Pd-C | 0.0 | 15 | 5 | 111 | 4.94 | 0.83 | 85.6 |
| 6 10% Pd-C | 0.167 | 30 | 5 | 143 | 16.04 | 1.71 | 90.6 |
| 7 10% Pd-C | 0.333 | 30 | 5 | 174 | 17.57 | 0.98 | 94.7 |
| 8 10% Pd-C | 0.500 | 30 | 5 | 169 | 17.40 | 0.38 | 97.9 |
| 9 10% Pd-C | 0.667 | 30 | 5 | 185 | 18.57 | TR (c) | >99.9 |

(a) 10% Pd-C = 1.0 gram; Pd(OAc)$_2$ =0.224 gram; CuCl$_2$ + 0.672 gram.
(b) IPA = isopropenyl acetate
(c) TR = trace
(d) at 65° C.

What we claim is:

1. A process for the preparation of allyl acetate which comprises first activating a supported palladium metal catalyst by contacting it with a C$_3$–C$_6$ olefin at a temperature of greater than about 50° C. for a period of time sufficient to provide at least a small but perceptible quantity of said activated catalyst, in the substantial absence of oxygen, and thereafter contacting the activated catalyst with acetic acid and propylene admixed with air or oxygen in a liquid medium, thereby forming allyl acetate.

2. A process for the preparation of allyl acetate which comprises first activating a supported palladium metal catalyst by contacting it with propylene in a liquid medium at a temperature of at least about 60° C. for at least about 10 minutes in the substantial absence of oxygen, and thereafter contacting the activated catalyst with acetic acid and additional propylene admixed with air or oxygen in said liquid medium, thereby forming allyl acetate.

3. The process of claim 1 or 2 wherein the catalyst is activated in the essential absence of oxygen.

4. The process of claim 1 or 2 wherein the catalyst is maintained in its activated state by continuous contact with propylene.

5. The process of claim 1 or 2 wherein the support for the palladium metal is carbon or alumina.

6. The process of claim 1 or 2 wherein the catalyst is activated with propylene under pressures of from about 1 to 100 atmospheres of propylene.

7. The process of claim 1 or 2 wherein the catalyst is activated with propylene at temperatures of from about 60° C. to 150° C. for at least about 10 to 120 minutes.

8. The process of claim 1 or 2 wherein the oxidation is carried out with not more than approximately stoichiometric amounts of oxygen needed to produce allyl acetate.

9. The process of claim 1 or 2 wherein the oxidation is carried out at temperatures of at least about 25° C.

10. The process of claim 1 or 2 wherein the oxidation is carried out in the added presence of sodium acetate.

11. The process of claim 1 or 2 wherein the oxidation is carried out in the added presence of acetic anhydride.

12. A process for the preparation of allyl acetate which comprises oxidizing propylene with air or oxygen in a liquid medium in the presence of acetic acid and an activated palladium metal catalyst, wherein said catalyst was previously activated by contacting a supported palladium metal catalyst with a C$_3$–C$_6$ olefin at a temperature of greater than about 50° C. for a period of time sufficient to provide at least a small but perceptible quantity of said activated catalyst, in the substantial absence of oxygen.

13. A process for the preparation of allyl acetate which comprises oxidizing propylene with air or oxygen in a liquid medium in the presence of acetic acid and an activated palladium metal catalyst, wherein said catalyst was previously activated by contacting a supported palladium metal catalyst in a liquid medium with propylene at a temperature of at least about 60° C. for at least about 10 minutes in the substantial absence of oxygen.

14. The process of claim 12 or 13 wherein the catalyst is activated in the essential absence of oxygen.

15. The process of claim 12 or 13 wherein the catalyst is maintained in its activated state by continuous contact with propylene.

16. The process of claim 12 or 13 wherein the support for the palladium metal is carbon or alumina.

17. The process of claim 12 or 13 wherein the catalyst is activated with propylene under pressures of from about 1 to 100 atmospheres of propylene.

18. The process of claim 12 or 13 wherein the catalyst is activated with propylene at temperatures of from about 60° C. to 150° C. for at least about 10 to 120 minutes.

19. The process of claim 12 or 13 wherein the oxidation is carried out with not more than approximately stoichiometric amounts of oxygen needed to produce allyl acetate.

20. The process of claim 12 or 13 wherein the oxidation is carried out at temperatures of at least about 25° C.

21. The process of claim 12 or 13 wherein the oxidation is carried out in the added presence of sodium acetate.

22. The process of claim 12 or 13 wherein the oxidation is carried out in the added presence of acetic anhydride.

23. The process of claim 1 or 12 wherein the C$_3$–C$_6$ olefin is propylene.

24. The process of claim 1 or 12 wherein the activation is carried out at a temperature of at least about 55° C.

25. The process of claim 1 or 12 wherein the activation is carried out in a liquid medium.

26. Process of claims 1 or 2 wherein the catalyst is activiated in the presence of acetic acid.

27. Process of claim 12 or 13 wherein the catalyst was activated in the presence of acetic acid.

28. Process of claims 1, 2, 12 or 13 wherein the oxidation is carried out in the added presence of a metal acetate.

29. Process of claims 1, 2, 12 or 13 wherein the oxidation is carried out at temperatures of from about 25°–85° C.

30. Process of claims 1, 2, 12 or 13 wherein the oxidation is carried out at temperatures of from about 25°–85° C. and not more than approximately stoichiometric amounts of oxygen.

* * * * *